(12) United States Patent  
Jeong et al.

(10) Patent No.: US 8,008,621 B2  
(45) Date of Patent: Aug. 30, 2011

(54) APPARATUS OF MEASURING THE ORIENTATION RELATIONSHIP BETWEEN NEIGHBORING GRAINS USING A GONIOMETER IN A TRANSMISSION ELECTRON MICROSCOPE AND METHOD FOR REVEALING THE CHARACTERISTICS OF GRAIN BOUNDARIES

(75) Inventors: Hi Won Jeong, Kyunsamgnam-do (KR); Seong Moon Seo, Kyunsamgnam-do (KR); Hyun Uk Hong, Kyunsamgnam-do (KR); Young Soo Yoo, Kyunsamgnam-do (KR); In Soo Kim, Kyunsamgnam-do (KR); Baig Gyu Choi, Kyunsamgnam-do (KR); Chang Yong Jo, Kyunsamgnam-do (KR)

(73) Assignee: Korea Institute of Machinery & Materials, Kyunsangnam-Do (KR)

( * ) Notice: Subject to any disclaimer, the term of this patent is extended or adjusted under 35 U.S.C. 154(b) by 271 days.

(21) Appl. No.: 12/343,853

(22) Filed: Dec. 24, 2008

(65) Prior Publication Data

US 2010/0019145 A1    Jan. 28, 2010

(30) Foreign Application Priority Data

Jul. 23, 2008 (KR) .................. 10-2008-0071414

(51) Int. Cl.  
    *G01N 23/00* (2006.01)
(52) U.S. Cl. ........................ 250/307; 250/311; 702/28
(58) Field of Classification Search .................... 250/307  
    See application file for complete search history.

(56) References Cited

U.S. PATENT DOCUMENTS

| | | | | |
|---|---|---|---|---|
| 4,247,771 A * | 1/1981 | Frevel | ............................ | 378/75 |
| 4,961,210 A * | 10/1990 | Fatemi | ............................ | 378/73 |
| 5,077,767 A * | 12/1991 | Gaukroger | ....................... | 378/73 |
| 5,179,280 A * | 1/1993 | Wang | ............................ | 250/311 |
| 5,235,523 A * | 8/1993 | Karen et al. | ..................... | 702/28 |
| 5,350,921 A * | 9/1994 | Aoyama et al. | ................ | 250/311 |
| 5,481,111 A * | 1/1996 | Rosar et al. | .................... | 250/311 |
| 6,923,171 B2 * | 8/2005 | Hammer et al. | ........... | 125/16.02 |

FOREIGN PATENT DOCUMENTS

| | | |
|---|---|---|
| JP | 5142168 A | 6/1993 |
| JP | 06103948 | 4/1994 |
| JP | 11288679 | 10/1999 |
| JP | 2000277044 | 10/2000 |
| JP | 2002279925 A | 9/2002 |
| JP | 2007200573 | 8/2007 |

* cited by examiner

*Primary Examiner* — Phillip A Johnston  
(74) *Attorney, Agent, or Firm* — Edell, Shapiro & Finnan, LLC (57) ABSTRACT

An apparatus and method for measuring the crystallographic orientation relationship of neighboring grains and the characteristics of grain boundaries using a goniometer of a transmission electron microscope are disclosed to check the orientation relationship between two crystals and the characteristics of grain boundaries with a small error in real time. An apparatus for measuring the orientation relationship between neighboring grains and the characteristics of grain boundaries by using a goniometer of a transmission electron stereoscope, the apparatus comprising a goniometer mounted at a transmission electron microscope and a measurement unit for revealing the characteristics of grain boundaries of a specimen by linear-algebraically interpreting the relationship between crystal axes and tilt axes of the specimen using the goniometer.

8 Claims, 8 Drawing Sheets

APPARATUS OF MEASURING THE ORIENTATION RELATIONSHIP BETWEEN NEIGHBORING GRAINS USING A GONIOMETER IN A TRANSMISSION ELECTRON MICROSCOPE AND METHOD FOR REVEALING THE CHARACTERISTICS OF GRAIN BOUNDARIES

CROSS REFERENCE TO RELATED APPLICATIONS

This application claims priority under 35 U.S.C. §119 to Application No. KR 10-2008-0071414 filed on Jul. 23, 2008, entitled "Apparatus of Measuring the Orientation Relationship Between Neighboring Grains Using a Goniometer in a Transmission Electron Microscope and Method for Revealing the Characteristics of Grain Bounderies," the entire contents of which are hereby incorporated by reference.

FIELD OF THE INVENTION

The present invention relates to an apparatus for measuring the orientation relationship between neighboring grains and a method for revealing the characteristics of grain boundaries using the same, and more particularly, to an apparatus for measuring the orientation relationship between neighboring grains using a goniometer in a transmission electron microscope and a method for revealing the characteristics of grain boundaries by using the apparatus.

BACKGROUND

A transmission electron microscope is a device that allows the observation of a crystal structure or a crystal defect with the interference between the transmitted electrons and the diffracted electrons caused by the incidence of electron beam into a few nm thick of specimen. In particular, the transmission electron microscope is advantageously used to investigate the crystal structure or the orientation relationship of crystal to recognize the characteristics of grain boundaries. The revelation of the characteristics of the grain boundaries using the transmission electron microscope in the related art was made by analyzing a Kikuchi pattern induced by inelastic scattering electrons.

However, in the related art method of revealing the characteristics of grain boundaries using the transmission electron microscope, the characteristics of the grain boundaries being found out by establishing a reference coordinate on the Kikuchi pattern-developed film and then measuring the angle and distance between crystal planes, it is difficult to reveal the characteristics of the grain boundaries in real time using the transmission electron microscope. In addition, an error is likely to be introduced in both establishing the reference coordinate on the Kikuchi pattern-developed film and determining the camera distance. Thus, the use of the Kikuchi pattern-developed film would result in much error in misorientation of two grains.

SUMMARY

Therefore, one object of the present invention is to provide an apparatus for measuring the orientation relationship between grains using a goniometer of a transmission electron microscope in order to find out the orientation relationship of neighboring grains and the characteristics of grain boundaries precisely in real time.

The other object of the present invention is to provide a method for measuring the characteristics of grain boundaries as well as the orientation relationship between grains using the apparatus.

To achieve the above objects, the present invention provides an apparatus for measuring the orientation relationship between neighboring grains, including: a goniometer mounted at a transmission electron microscope; and a measurement unit for revealing the characteristics of grain boundaries by establishing the linear-algebraic relationship between crystal axes and tilting axes of the specimen by measuring the tilt angles using a goniometer mounted on a transmission electron microscope.

In the present invention, the relationship between the crystal axis (or crystal lane, for example, H5, H6, H7 which are estimated from the measured crystal axes of H1, H2, H3), and the tilt axes of the specimen (Tx, Ty, Tz) is described by linear algebra with respect to Cartesian coordinate system; a Tx [100] axis and a Ty [010] axis perpendicular to an X tilt axis and a Y tilt axis, respectively, mounted on a transmission electron microscope and a Tz [001] axis perpendicular to the Tx axis and the Ty axis being related to the crystal axes of H5, H6, and H7.

To achieve the above objects, the present invention provides a method for measuring the misorientation between grains. In the method, the indices of crystal axes H1, H2, and H3 are determined by the diffraction pattern first. Then three of angle pairs Tx's and Ty's corresponding to the respective crystal axes H1, H2, and H3 are measured. Subsequently, the three interplanar angles between H1 and H2, between H2 and H3, between H3 and H1 are calculated using the measured angle pairs of (Tx, Ty) on the respective crystal axes of H1, H2, and H3. Thereafter, three interplanar angles among H1, H2, and H3 are calculated according to a crystallography method. Thereafter, the (Tx, Ty) angle pairs which show minimized difference between the measured interplanar angles and the crystallographically calculated interplanar angles are adopted as precisely measured angles of Tx's and Ty's to establish the correspondence matrix between the tilt axes of Tx, Ty, Tz, and the crystal axes of H5, H6, H7. Subsequently, a misorientation matrix between two crystals is obtained. And then, the characteristics of grain boundaries are revealed by using the misorientation matrix.

In a preferred embodiment of the present invention, the minimizing of the difference between the measured interplanar angles among the crystal axes H1, H2, and H3 and the calculated interplanar angles may include: obtaining the interplanar angles among the crystal axes H1, H2, and H3 using the measured angle pairs of (Tx, Ty); and determining indices of the measured crystal axes H1, H2, and H3 and calculating the interplanar angles of a cubic system from the indices of H1, H2, H3 crystallographically. The principle of obtaining the interplanar angles among the crystal axes H1, H2, and H3 from the measured angle pairs of (Tx, Ty) is same as a principle of obtaining an angle (γ) inclined from a centered transmitted beam when inclined by a tilt angle (α) along the Tx axis and subsequently inclined by a tilt angle (β) along the Ty axis.

The establishing of the relationship between the tilt axes and the crystal axes H5, H6, and H7 may include: estimating an arbitrary crystal axis H4 from the crystal axes H1, H2, and H3.

In the method for measuring the misorientation between grains according to the present invention, the correspondence matrix between the tilt axes of Tx, Ty, and Tz and the crystal axes may be established by finding out the crystal axes of H5, H6, and H7 parallel with the tilt axes of Tx [100], Ty [010], and Tz [001], respectively. The crystal axes of H5, H6, and H7 parallel with tilt axes of Tx [100], Ty [010], and Tz [001] are found out by the method of estimating an arbitrary crystal axis of H4 from the measured crystal axes of H1, H2, and H3. Alternatively, the corresponding matrix between the tilt axes and the crystal axes may be established by finding out both two crystal axes of H8, and H9 which are rotated by a certain angles of θ along Tx axis, and Ty axis, respectively, and one crystal axis of H7 parallel with Tz [001] axis. Both two crystal axes of H8, H9 and one crystal axis of H7 are found out by the method of estimating an arbitrary crystal axis of H4 from the measured crystal axes of H1, H2, and H3. Alternatively, the relationship between the tilt axes and the crystal axes may be established by two vectors of H10, H11 and one vector of H12. Two vectors of H10, H11 are obtained by subtracting a crystal axis vector parallel with the Tz axis from crystal axis vectors of H8, and H9 which are rotated by a certain angle θ along Tx axis, and Ty axis, respectively. One vector is parallel with Tz tilt axis. In this case, the certain angle θ may be larger than 0 but smaller than 10. Alternatively, the relationship between the tilt axes and the crystal axes may be established by two vectors and one vector. Two vectors are parallel components with Tx, and Ty, respectively in the subtracted vectors of the H10, H11. One vector is parallel with Tz tilt axis.

According to the apparatus for measuring the orientation relationship between neighboring grains using the goniometer of the transmission electron microscope of the present invention, the characteristics of the grain boundaries are revealed by linear-algebraic relationship between the crystal axes and the tilt axes of the specimen. Thus, the orientation relationship between the neighboring grains and the characteristics of the grain boundaries can be checked with a small error in real time.

The foregoing and other objects, features, aspects and advantages of the present invention will become more apparent from the following detailed description of the present invention when considering the accompanying drawings.

DETAILED DESCRIPTION

Exemplary embodiments of the present invention will now be described based upon the accompanying drawings. The following embodiments may be modified variably, and the scope of the present invention is not limited to those embodiments. The embodiments of the present invention are provided to perfectly explain the present invention to the skilled person in the art.

The present invention relates to an apparatus and method for measuring the orientation relationship between neighboring grains using a goniometer of a transmission electron microscope and revealing the characteristics of grain boundaries in a linear algebraic manner. In detail, in the present invention, the characteristics of grain boundaries are revealed by establishing the linear algebraic relationship between crystal axes and tilt axes of a specimen using the goniometer mounted at the transmission electron microscope, without directly using the related art of Kikuchi pattern. Accordingly, in the present invention, the characteristics of the grain boundaries can be found out in real time using the goniometer mounted at the transmission electron microscope.

Hereinafter, establishing the relationship between tilt axes and crystal axes using the goniometer, concerned with a crystal (referred to as a 'specimen', hereinafter) desired to be observed mounted thereon and then estimating an unknown crystal axes using the relationship will be described sequentially. In addition, the estimating method will be described in detail by stages.

Figure 1:
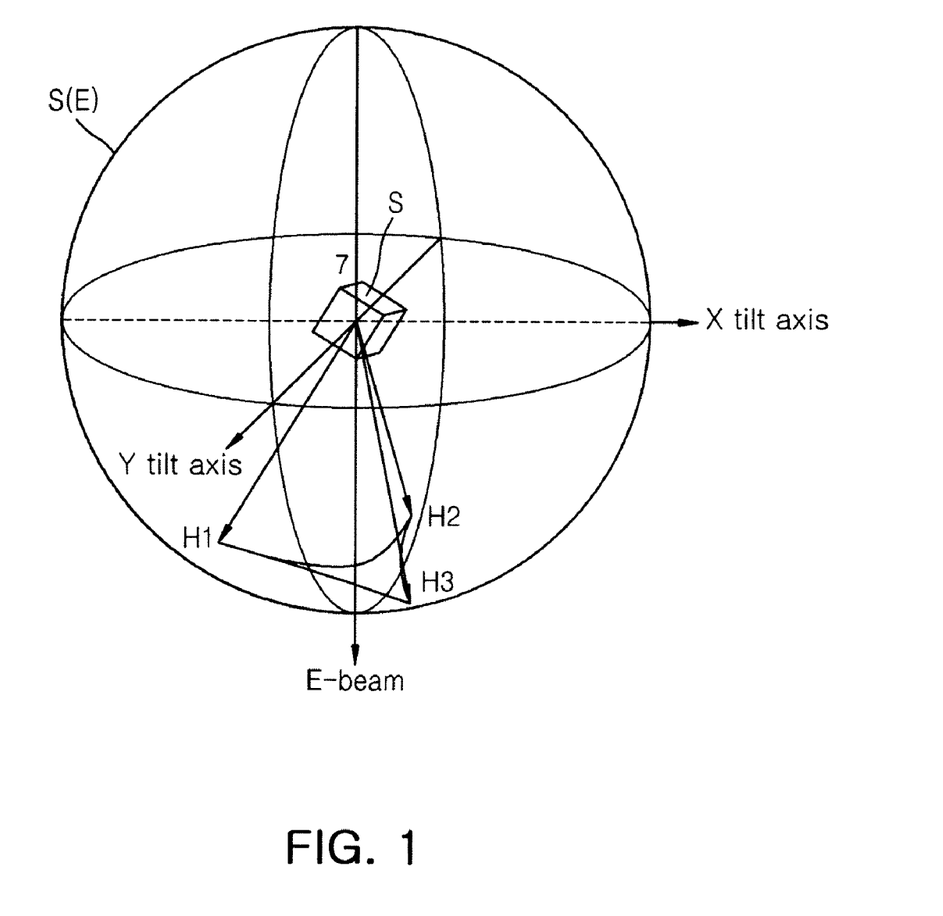
FIG. 1 is a drawing illustrating the relationship between tilt axes and crystal axes of a specimen mounted at a transmission electron microscope according to the present invention.
Figure 2:
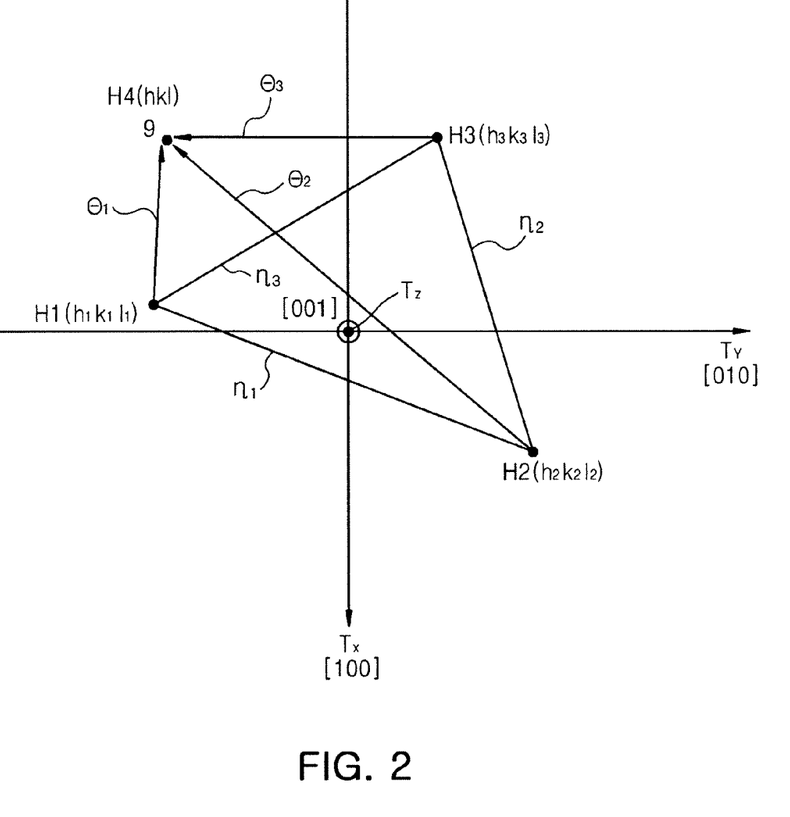
FIG. 2 is a drawing illustrating a linear algebraic method for estimating an arbitrary unknown crystal axis using the relationship between the three measured crystal axes and the tilt axes.

FIG. 1 is a drawing illustrating the relationship between tilt axes and crystal axes of the specimen mounted at the transmission electron microscope according to the present invention, and FIG. 2 is a drawing illustrating a linear algebraic method for estimating an unknown crystal axis using the relationship between the three measured crystal axes and the tilt axes. In this case, the goniometer is positioned between an objective lens and a condenser lens of the transmission electron microscope and has the specimen mounted thereon.

With reference to FIG. 1, there are shown crystal axes H1, H2, and H3 at which an electron beam (E-beam) is diffracted by a crystal plane after passing through the specimen mounted on the goniometer of the transmission electron microscope. Namely, the specimen (S) is positioned where an X tilt axis and a Y tilt axis of an Ewald sphere S(E) in a reciprocal space meet. Subsequently, when the E-beam is irradiated toward the specimen (S), the crystal axes of H1, H2, and H3 diffracted by the corresponding crystal plane of the specimen (S) can be checked from a screen of the transmission electron microscope. In this case, the crystal axis of H1 is a $(h_1k_1l_1)$ crystal axis (or crystal plane) diffracted by the corresponding crystal plane of the specimen (S), the crystal axis of H2 is a $(h_2k_2l_2)$ crystal axis, and the crystal axis of H3 is a $(h_3k_3l_3)$ crystal axis.

With reference to FIG. 2, an unknown crystal axis of H4 desired to be estimated can be found out using the algebraic relationship between the measured crystal axes of H1, H2, H3 and the tilt axes of Tx, Ty, Tz mounted on the transmission electron microscope. In detail, when the measured crystal axes of H1, H2, and H3 are disposed on the coordinates formed by a Tx axis and a Ty axis, which are perpendicular to the X tilt axis and the Y tilt axes mounted on the transmission electron microscope, interplanar angles $(\eta_1,\eta_2,\eta_3)$ among the crystal axes of H1, H2, and H3 can be obtained, respectively. In this case, $\eta_1$ is an interplanar angle between the H1 $(h_1k_1l_1)$ and H2 $(h_2k_2l_2)$, $\eta_2$ is an interplanar angle between the H2 $(h_2k_2l_2)$ and the H3 $(h_3k_3l_3)$, and $\eta_3$ is an interplanar angle between the H3 $(h_3k_3l_3)$ and H1 $(h_1k_1l_1)$. Before estimating an unknown crystal axis from the measure ones of H1, H2, H3, a process for obtaining the precise angle pairs of (Tx, Ty) on the corresponding H1, H2, H3. The process (S20) for the precise angle pairs will be described after describing the estimation of an unknown crystal axis of H4. On the other hand, interplanar angles of $\theta_1$, $\theta_2$, and $\theta_3$ between the H4 (hkl) desired to be estimated and the crystal axes H1, between the H4 and the H2, and between the H4 and the H3, respectively, can be obtained using the measured angle pairs of (Tx, Ty) on the crystal axes of H1, H2, H3. In this case, Tx axis and Ty axis are perpendicular to a Tz axis. The crystal axis of H4 desired to be estimated can be obtained using the relationship between the measured interplanar angles of $\theta_1$, $\theta_2$, $\theta_3$ and the crystallographic interplanar angles of $\theta_1$, $\theta_2$, $\theta_3$ as shown in equations (3), and (4). The measured interplanar angles of $\theta_1$, $\theta_2$, $\theta_3$ are obtained from the measured angle pairs of (Tx, Tz) on H1, H2, H3 and the angle pair of (Tx, Tz) on H4 desired to be estimated. For example when the angle pairs of (Tx, Tz) on H1 and H4 are (10, 20), and (0, 90), the interplanar angle of $\theta_1$ can be obtained from the difference of (−10, 70) between the H1 and the H4 using equation (4). The crystallographically determined interplanar angles of $\theta_1$, $\theta_2$, $\theta_3$ are obtained from the known indices of $(h_1k_1l_1)$ $(h_2k_2l_2)$, $(h_3k_3l_3)$ on the corresponding crystal plane of H1, H2, H3 and an unknown indices of (hkl) on the corresponding crystal plane of H4 using equation (3).

Figure 3:
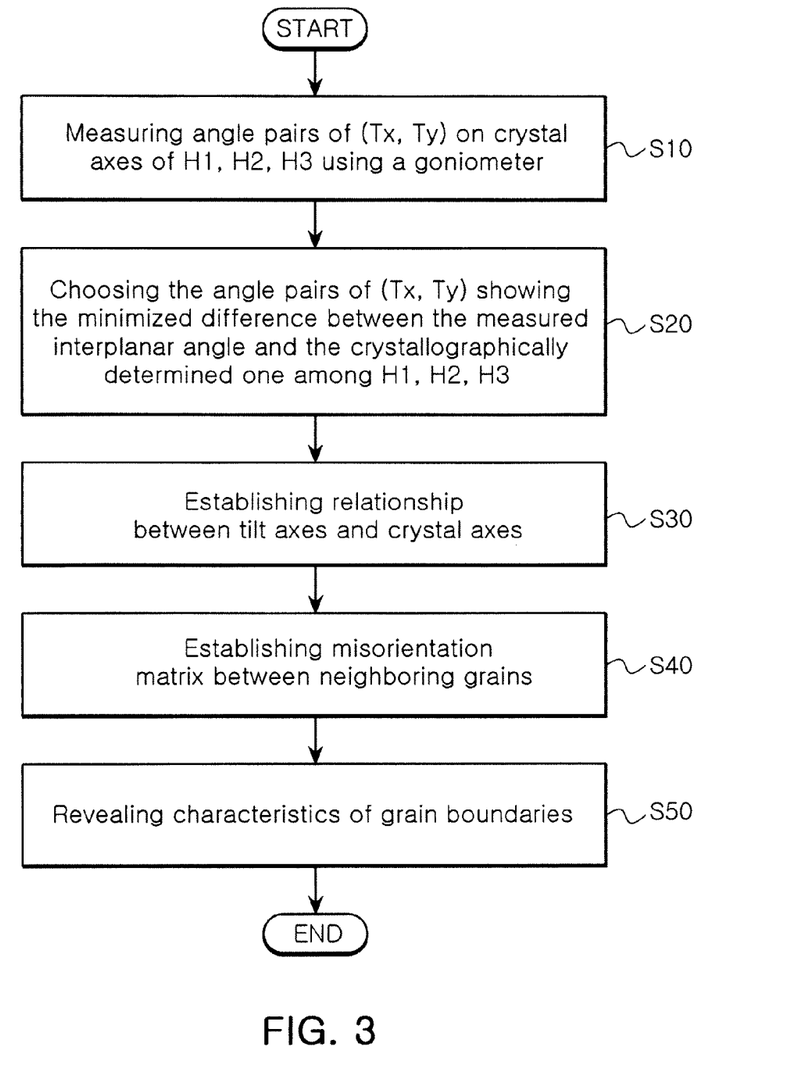
FIG. 3 is a flow chart illustrating the process of revealing the characteristics of grain boundaries according to the present invention.

FIG. 3 is a flow chart illustrating the process of revealing the characteristics of the grain boundaries according to the present invention.

With reference to FIG. 3, (Tx, Ty) angle pairs of the respective crystal axes of H1, H2, and H3 are measured using the goniometer in order to measure the interplanar angles ($\eta_1$, $\eta_2$, $\eta_3$) among the crystal axes H1, H2, and H3 (S10). And then, a measured angle pairs of (Tx, Ty) are chosen as a precise measured angle pairs which minimizing the difference between the measured interplanar angles and the crystallographically-calculated interplanar angles among the crystal axes of H1, H2, and H3 (S20). Subsequently, the relationship between a basis vectors of the tilt axes and that of the crystal axes are established (S30), and then, a misorientation matrix between two crystals is acquired (S40). Finally, the characteristics of grain boundaries are revealed using the acquired misorientation matrix (S50). Hereinafter, the process of revealing the characteristics of the grain boundaries will now be described by stages.

Measuring of the Crystal Axes H1, H2, and H3 (S10)

The three crystal axes of H1, H2, and H3 in a crystal desired to be observed are measured using the goniometer as shown in FIGS. 1 and 2. In detail, the specimen ('S' in FIG. 1) is inclined to find out a crystal axis parallel to the direction of the transmitted E-beam in FIG. 1, and the angle pairs of (Tx, Ty) indicated at the goniometer at that time are recorded. This process is performed for every grain desired to be observed. For example, if two grains (A and B) are discriminated by a grain boundary, the respective angle pairs (Tx, Ty) of the crystal axes $H(A)1(h_1k_1l_1)$, $H(A)2(h_2k_2l_2)$, and $H(A)3 (h_3k_3l_3)$ of the grain 'A' and $H(B)1(h_1k_1l_1)$, $H(B)2(h_2k_2l_2)$, and $H(B)3(h_3k_3l_3)$ of the grain 'B' are all measured.

Evaluating of the Accuracy of Measured Values (S20)

In case of the grain 'A', the interplanar angles among the crystal axes of $H(A)1$, $H(A)2$, and $H(A)3$ are calculated by equation (1) using the measured angle pairs of (Tx, Ty) on the crystal axes of $H(A)1$, $H(A)2$, and $H(A)3$. Subsequently, the interplanar angles among the crystal axes of $H(A)1$, $H(A)2$, $H(A)3$ are calculated by equation (2) using the miller indices of $(h_1k_1l_1)$, $(h_2k_2l_2)$, $(h_3k_3l_3)$ on the corresponding crystal axes of $H(A)1$, $H(A)2$, and $H(A)3$. The angle pairs of (Tx, Ty) are chosen as the precise angle pairs which make the difference between the measured interplanar angle and the crystallographically determined interplanar angle as small as possible. The reason is because if the difference between the measured interplanar angle based upon the three crystal axes and the crystallographically calculated angle is large, the orthogonality of the Cartesian coordinate system is degraded to result in much error in the estimated crystal axis H4. The tilt angle pairs of (Tx, Ty) on the related crystal axes are measured several times and a (Tx, Ty) angle at which the difference between the measured interplanar angles and the calculated interplanar angles is as small as possible is selected to thereby improve the orthogonality of the Cartesian coordinate system to its maximum level.

Figure 4:
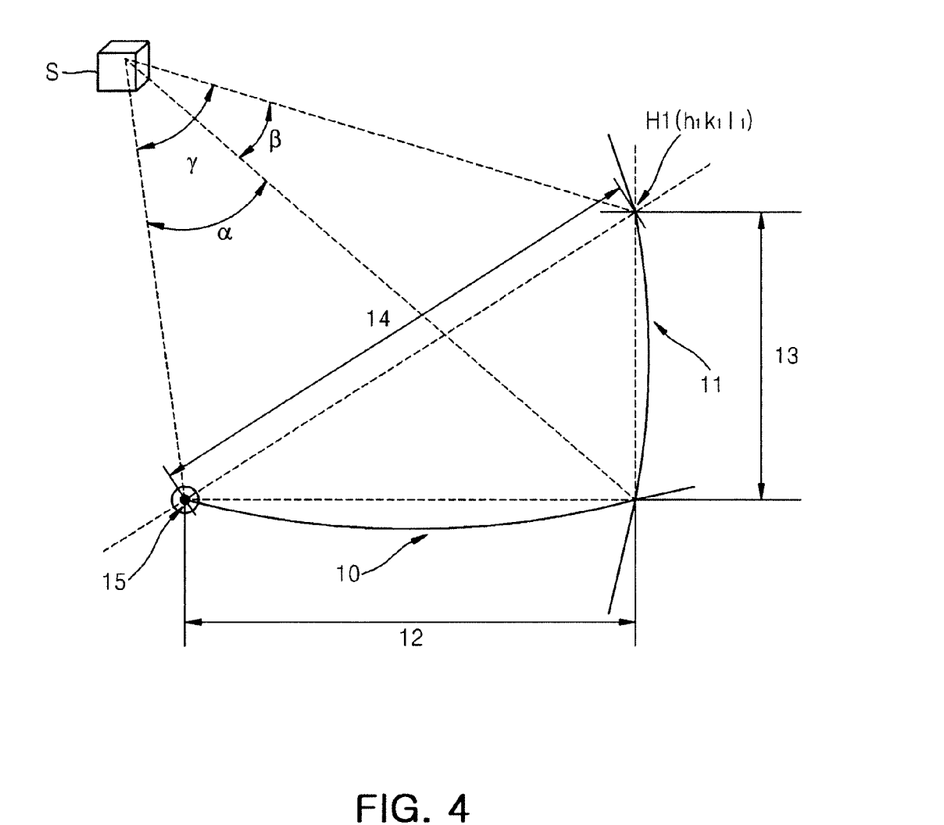
FIG. 4 is a drawing illustrating a method for calculating interplanar angles of the crystal axes using the measured angle pairs of (Tx, Ty) as a portion of FIG. 1.

FIG. 4 is a drawing illustrating a method for calculating the interplanar angles ($\eta_1$, $\eta_2$, $\eta_3$) among the crystal axes of $H(A)$ 1, $H(A)2$, $H(A)3$ using the (Tx, Ty) angle pairs measured by the goniometer as a portion of FIG. 1. Here, FIG. 4 is expressed by the trace 10 of the crystal axes on the Ewald sphere S(E) formed by X tilting, a trace 11 of the crystal axes on the Ewald sphere S(E) formed by Y tilting, the distance 12 along the Tx axis associated with the X tilt angle ($\alpha$), the distance 13 along the Ty axis associated with the Y tilt angle ($\beta$), and the combined distance 14 associated with a total tilt angle ($\gamma$) induced by the X tilt angle ($\alpha$) and the Y tilt angle ($\beta$). Reference numeral 15 denotes a centered E-beam.

In more detail, when the crystal axis $H(A)1(h_1k_1l_1)$ is inclined by the tilt angle ($\alpha$) along the Tx axis related to the X tilting and the tilt angle ($\beta$) along the Ty axis related to the Y tilting, the total tilt angle ($\gamma$) inclined from the centered beam 15 has the following relationship:

$$\cos \gamma = \cos \alpha + \cos \beta - 1 \qquad \text{Equation (1)}$$

Namely, the interplanar angles ($\eta_1$, $\eta_2$, $\eta_3$) among the three crystal axes of $H(A)1$, $H(A)2$, and $H(A)3$ can be all obtained by equation (1) based upon the carefully measured (Tx, Ty) angle pairs using the goniometer.

In addition, the interplanar angles between the crystal axes $H(A)1(h_1k_1l_1)$, and $H(A)2(h_2k_2l_2)$ of the cubic system can be calculated by the crystallographic formula shown below:

$$\cos \eta_1 = \frac{h_1 h_2 + k_1 k_2 + l_1 l_2}{\sqrt{h_1^2 + k_1^2 + l_1^2} \sqrt{h_2^2 + k_2^2 + l_2^2}} \qquad \text{Equation (2)}$$

Moreover, the interplanar angles of ($\eta_1$, $\eta_2$, $\eta_3$) in grain B can be obtained by equation (1) using the measured angle pairs of $(Tx_1, Ty_1)$, $(Tx_2, Ty_2)$, $(Tx_3, Ty_3)$ on $H(B)1$, $H(B)2$, and $H(B)3$ with respect to the grain 'B', and the crystallographically calculated interplanar angles among $H(B)1$, $H(B)$ 2, and $H(B)3$ can be obtained by equation (2). In this respect in measuring the interplanar angles among the three crystal axes with respect to the grain 'B', three crystal axes of $H(B)1$, $H(B)2$, and $H(B)3$ may be chosen which are as close as possible to the centered transmitted E-beam. Through this process, the orthogonality of the Cartesian coordinate system can be improved.

Establishing of the Relationship Between the Tilt Axes and the Crystal Axes (S30)

Here, accurately measuring the angles between the three crystal axes of $H(A)1$, $H(A)2$, and $H(A)3$ and estimating the arbitrary crystal axis $H(A)4$ desired to be known from the three crystal axes of $H(A)$ 1, $H(A)2$, and $H(A)3$ are also included. The arbitrary crystal axis $H(A)4$(h k l) in FIG. 2 can be calculated by equation (3) shown below:

$$\begin{pmatrix} h'_1 & k'_1 & l'_1 \\ h'_2 & k'_2 & l'_2 \\ h'_3 & k'_3 & l'_3 \end{pmatrix} \begin{pmatrix} h \\ k \\ l \end{pmatrix} = \begin{pmatrix} \cos\theta_1 \\ \cos\theta_2 \\ \cos\theta_3 \end{pmatrix} \qquad \text{Equation (3)}$$

wherein h'i=hi/$\sqrt{hi^2+ki^2+li^2}$, k'i=ki/$\sqrt{hi^2+ki^2+li^2}$, l'i=li/$\sqrt{hi^2+ki^2+li^2}$, i=1, 2, 3. The angles of $\theta_1$, $\theta_2$, and $\theta_3$ have the following relationship with the tilt angles:

$$\begin{pmatrix} \cos\theta_1 \\ \cos\theta_2 \\ \cos\theta_3 \end{pmatrix} = \begin{pmatrix} \cos\Delta Tx_1 + \cos\Delta Ty_1 - 1 \\ \cos\Delta Tx_2 + \cos\Delta Ty_2 - 1 \\ \cos\Delta Tx_3 + \cos\Delta Ty_3 - 1 \end{pmatrix} \qquad \text{Equation (4)}$$

wherein the differences between ($Tx_1$, $Ty_1$) corresponding to H(A)1($h_1k_1l_1$), and ($Tx_4,Ty_4$) corresponding to H(A)4(h k l), between ($Tx_2,Ty_2$) corresponding to H(A)2($h_2k_2l_2$), and ($Tx_4,Ty_4$), between ($Tx_3,Ty_3$) corresponding to H(A)3 ($h_3k_3l_3$) and ($Tx_4,Ty_4$) are ($\Delta Tx_1$, $\Delta Ty_1$), ($\Delta Tx_2$, $\Delta Ty_2$), ($\Delta Tx_3$, $\Delta Ty_3$), respectively.

Figure 5:
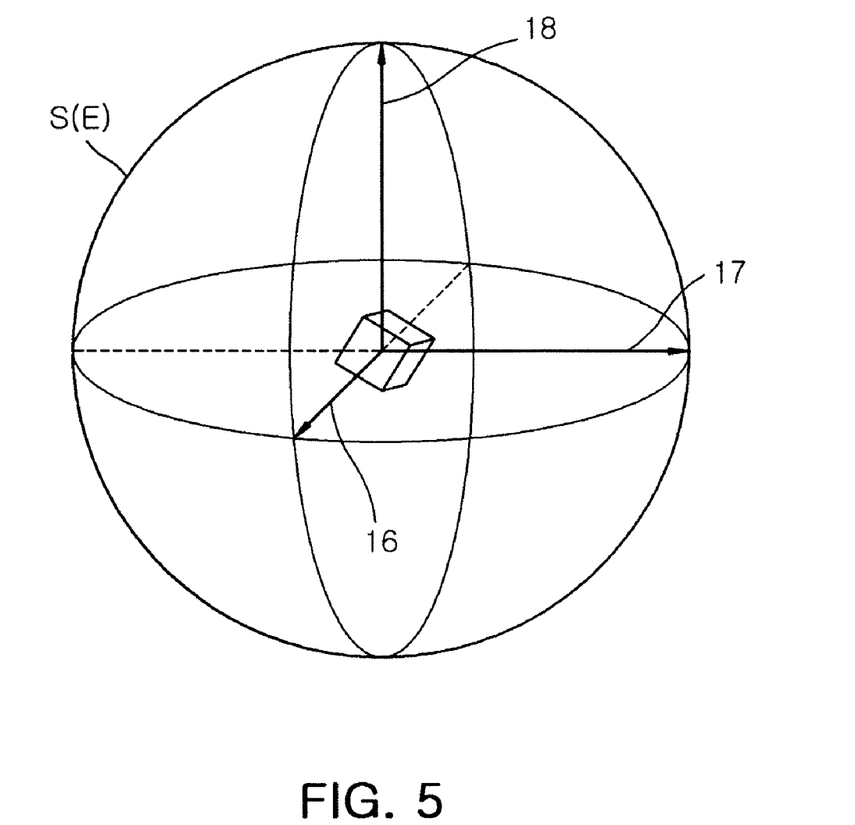
FIG. 5 is a conceptual view of a first method for establishing the relationship between the crystal axes and the tilt axes.

There are three methods of establishing the relationship between the crystal axes and the tilt axes using the estimated crystal axes calculated by the relationship between equation (3) and equation (4). Namely, a first method is using the crystal axes when H5(Tx=90, Ty=0)(16), H6(Tx=0, Ty=90)(17), and H7(Tx=0, Ty=0)(18) as shown in FIG. 5. In this case, the crystal axis of H5(Tx=90, Ty=0)(16) is parallel with [100] axis of the tilt axis, the crystal axis of H6(Tx=0, Ty=90)(17) is parallel with [010] axis of the tilt axis, and the crystal axis of H7(Tx=0, Ty=0)(18) is parallel with [001] axis of the tilt axis.

A second method is to use both two crystal axes rotated by an angle $\theta$ along Tx axis and Ty axis, respectively and one crystal axis parallel with Tz. The crystal axes rotated by an angle $\theta$ can be calculated using equation (3) and equation (4). For example, the values inputted to equation (3) and equation (4) may be H8(Tx=10, Ty=0)(19), H9(Tx=0, Ty=10)(20), H7(Tx=0, Ty=0)(21), respectively, and the crystal axes at this time are calculated, respectively. In this case, the crystal axis of H8(Tx=10, Ty=0)(19) is arranged to be parallel to [x0z] axis of the tilt angle, the crystal axis of H9(Tx=0, Ty=10)(20) is arranged to be parallel to [0yz] axis of the tilt angle, and the crystal axis of H7(Tx=0, Ty=0)(21) is arranged to be parallel to [001] axis. In this case, the value of $\theta$ may be an arbitrary value which is larger than 0 but smaller than or the same as 10, and preferably, a value with good orthogonality of misorientation matrix may be selected from the corresponding range.

A third method is that crystal axes vectors when rotated by a same arbitrary angle $\theta$ along the X axis and along the Y axis are calculated using equation (3) and equation (4), and then three crystal axes vectors obtained by subtracting a crystal axis vector parallel to the Tz from the rotated crystal axes vectors are used. For example, (Tx=10, Ty=0), (Tx=0, Ty=90), (Tx=0, Ty=0) being substituted as input values to equation (3) and equation (4), corresponding crystal axes are obtained, and a crystal axis when (Tx=0, Ty=0) is subtracted from the corresponding crystal axes of (Tx=10, Ty=0) and (Tx=0, Ty=10), respectively.

Figure 7:
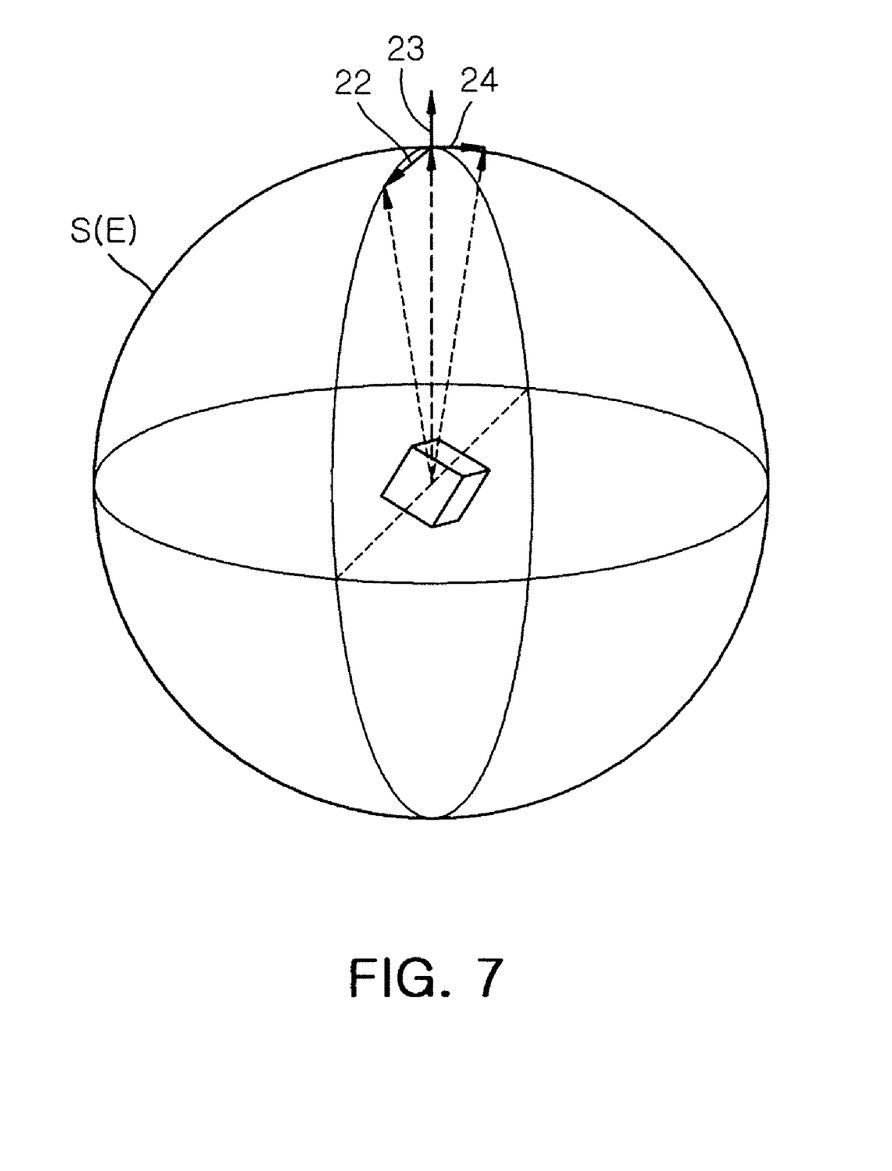
FIG. 7 is a conceptual view of a third method for establishing the relationship between the crystal axes and the tilt axes.

In more detail, reference numeral 22 in FIG. 7 denotes a crystal axis H10, which is obtained by subtracting the crystal axis of (Tx=0, Ty=0) from the crystal axis when (Tx=10, Ty=0), arranged to be approximately parallel to [100] axis of the tilt axis, reference numeral 24 denotes a crystal axis H11, which is obtained by subtracting the crystal axis of (Tx=0, Ty=0) from the crystal axis when (Tx=0, Ty=10), arranged to be approximately parallel to [010] axis of the tilt axis, and reference numeral 23 denotes a crystal axis H12, when (Tx=0, Ty=0), arranged to be parallel to [001] axis of the tilt axis. In this case, the value $\theta$ may be an arbitrary value which is larger than 0 but smaller than or the same as 10, and preferably, a value with good orthogonality of orthogonal coordinates may be selected from the corresponding range.

The fourth method is to use two vectors having parallel component to the direction of Tx[100], Ty[010], and one vector parallel to the Tz[001] in the subtracted vectors at the third method.

The first method will now be described in detail with reference to FIG. 5. the crystal axes of H5(Tx=90, Ty=0)(16), H6(Tx=0, Ty=90)(17), and H7(Tx=0, Ty=0)(18) are calculated by using the relationships of equation (3) and equation (4), respectively, and the following correspondence matrix ($c_iMt$) is established for the relationship between the basis vector of the crystal axes and that of the tilt axes. In this case, the correspondence matrix is established for all the grains $c_i$ desired to be observed. When the grains 'A' and 'B' are assumed, 'i' indicates 'A' and 'B'.

$$(c_iMt) = \begin{pmatrix} h_{Tx=90,Ty=0} & h_{Tx=0,Ty=90} & h_{Tx=0,Ty=0} \\ k_{Tx=90,Ty=0} & k_{Tx=0,Ty=90} & k_{Tx=0,Ty=0} \\ l_{Tx=90,Ty=0} & l_{Tx=0,Ty=90} & l_{Tx=0,Ty=0} \end{pmatrix} \qquad \text{Equation (5)}$$

In the first method, when three crystal axes are precisely measured, the accurate values can be expressed mathematically. However, the crystal may be bent or rotated because the specimen is so thin, and the three crystal axes cannot be measured with respect to the same zone axis, so it is not possible to precisely measure the three crystal axes. This results in an inevitable error. Such error may be discriminated by an angle between the three crystal axis calculated by equation (1) and equation (2). Thus, although the first method is the most accurate method in linear algebraic aspect, it is disadvantageous in that the orthogonality of the Cartesian coordinate system deteriorates because of the inevitable error in measuring the tilt angles with respect to the three crystal axes.

Figure 6:
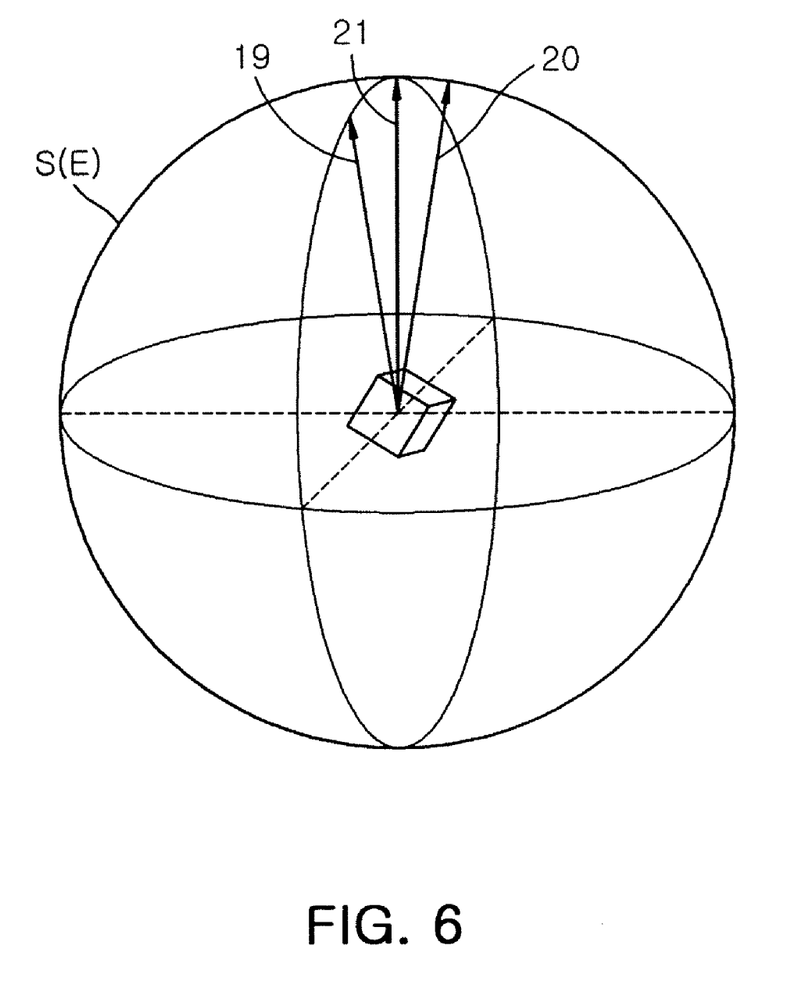
FIG. 6 is a conceptual view of a second method for establishing the relationship between the crystal axes and the tilt axes.

The second method aims to improve the orthogonality of the misorientation matrix. In this method, the crystal axes rotated by the same arbitrary angle of $\theta$, along the X axis and along the Y axis as shown in FIG. 6 are used, and the crystal axes obtained by rotating by the angle $\theta$ can be calculated using equation (3) and equation (4). For example, the crystal axes of H8(Tx=10, Ty=0)(19), H9(Tx=0, Ty=10)(20), and H7(Tx=0, Ty=0)(21) are calculated, respectively, to establish the following correspondence matrix. In this case, the correspondence matrix is established for all the grains $c_i$ desired to be observed. When the grains 'A' and 'B' are assumed, 'i' indicates 'A' and 'B'. In this case, the value $\theta$ may be an arbitrary value which is larger than 0 but smaller than or the same as 10, and preferably, a value with good orthogonality of misorientation matrix may be selected from the corresponding range.

$$(c_iMt) = \begin{pmatrix} h_{Tx=\theta,Ty=0} & h_{Tx=0,Ty=\theta} & h_{Tx=0,Ty=0} \\ k_{Tx=\theta,Ty=0} & k_{Tx=0,Ty=\theta} & k_{Tx=0,Ty=0} \\ l_{Tx=\theta,Ty=0} & l_{Tx=0,Ty=\theta} & l_{Tx=0,Ty=0} \end{pmatrix} \qquad \text{Equation (6)}$$

The third method aims to improve the orthogonality of the crystal axes and the tilting axes. In this method, elements of matrix of the established equation (6) are used. The values obtained by rotating by the same arbitrary angle of θ along the X axis and along the Y axis as shown in FIG. 7 are used, and the values obtained by rotation of the angle θ can be calculated using equation (3) and equation (4). For example, the crystal axes H8(Tx=10, Ty=0)(19), H9(Tx=0, Ty=10)(20), and H7(Tx=0, Ty=0)(21) are calculated, respectively, to establish the correspondence matrix of equation (6). The crystal axis H10 obtained by subtracting the indices of crystal axes at (Tx=0, Ty=0) from those at (Tx=10, Ty=0) is arranged to be parallel with [100] axis of the tilt axis in the established elements of matrix of equation (6), the crystal axis H11 obtained by subtracting the indices of crystal axes at (Tx=0, Ty=0) from those at (Tx=0, Ty=10) is arranged to be parallel with [010] axis of the tilt axis, and the crystal axis H12 when (Tx=0, Ty=0) is arranged to be parallel with [001] axis of the tilt axis, to thus establish the correspondence matrix. In this case, the value θ may be an arbitrary value which is larger than 0 but smaller than or the same as 10, and preferably, a value with good orthogonality of orthogonal coordinates may be selected from the corresponding range.

The third method features that the elements of the correspondence matrix are closely parallel to the direction of Tx[100], Ty[010], and Tz[001], so good orthogonality can be obtained between the crystal axes and the tilting axes. This orthogonality has even more improved characteristics than that of the second method in terms of the linear algebraic aspect.

$$(c_i M t) = \begin{pmatrix} h_{Tx=\theta,Ty=0} & -h_{Tx=0,Ty=0} & h_{Tx=0,Ty=\theta} & -h_{Tx=0,Ty=0} & h_{Tx=0,Ty=0} \\ k_{Tx=\theta,Ty=0} & -k_{Tx=0,Ty=0} & k_{Tx=0,Ty=\theta} & -k_{Tx=0,Ty=0} & k_{Tx=0,Ty=0} \\ l_{Tx=\theta,Ty=0} & -l_{Tx=0,Ty=0} & l_{Tx=0,Ty=\theta} & -l_{Tx=0,Ty=0} & l_{Tx=0,Ty=0} \end{pmatrix}$$

Equation (7)

Figure 8:
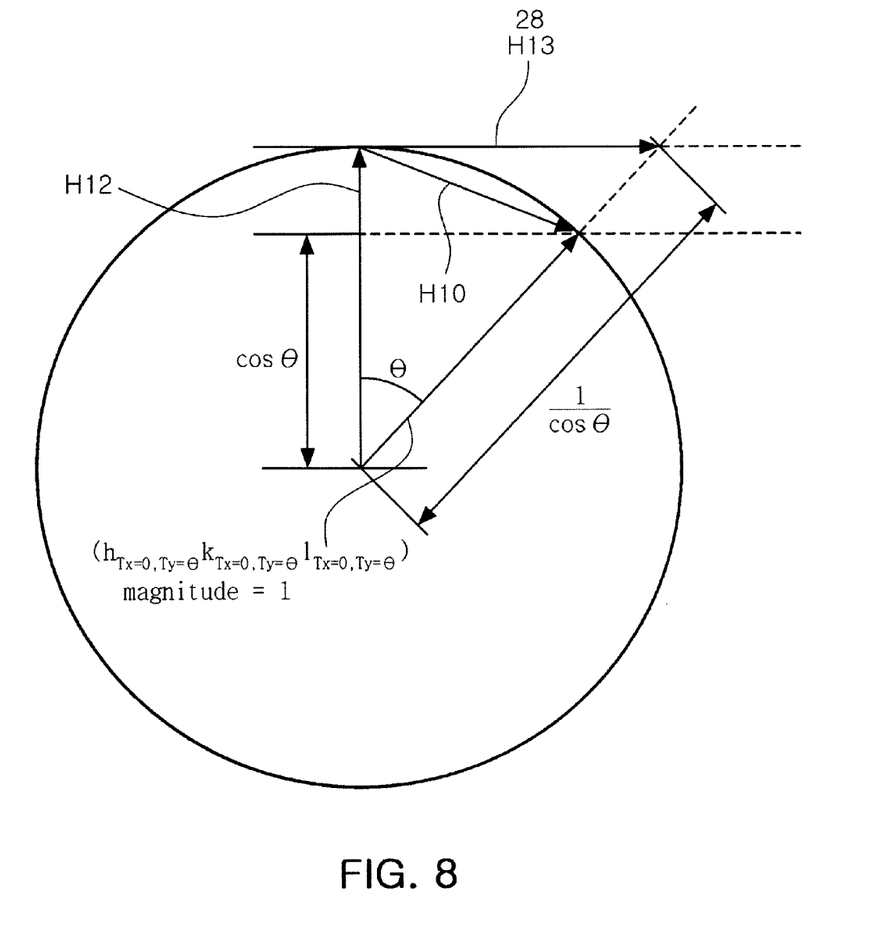
FIG. 8 is a conceptual view of a fourth method for establishing the relationship between the crystal axes and the tilt axes.

The fourth method features that the elements of the correspondence matrix is composed of the parallel component to the direction of Tx[100], Ty[010], and Tz[001] in the subtracted vectors at the third method. The crystal axis, ($a_{11}$ $a_{12}$ $a_{13}$), which is parallel component to Tx axis in the vector obtained by subtracting the indices of crystal axes at (Tx=0, Ty=0) from those at (Tx=θ, Ty=0), is expressed as equation (8) using the geometry as shown in FIG. 8.

$$a_{11} = \frac{h_{Tx=\theta,T_y=0}}{\cos\theta} - h_{Tx=0,Ty=0}$$

$$a_{12} = \frac{k_{Tx=\theta,T_y=0}}{\cos\theta} - k_{Tx=0,Ty=0}$$

$$a_{11} = \frac{l_{Tx=\theta,T_y=0}}{\cos\theta} - l_{Tx=0,Ty=0}$$

Equation (8)

The crystal axis, ($b_{11}$ $b_{12}$ $b_{13}$), which is parallel component to Ty axis in the vector obtained by subtracting the indices of crystal axes at (Tx=0, Ty=0) from those at (Tx=0, Ty=θ), is expressed as equation (9) in similar manner.

$$b_{11} = \frac{h_{Tx=0,T_y=\theta}}{\cos\theta} - h_{Tx=0,Ty=0}$$

Equation (9)

$$b_{12} = \frac{k_{Tx=0,T_y=\theta}}{\cos\theta} - k_{Tx=0,Ty=0}$$

$$b_{13} = \frac{l_{Tx=0,T_y=\theta}}{\cos\theta} - l_{Tx=0,Ty=0}$$

Eventually, the relationship matrix can be established as follows:

$$(c_i M t) = \begin{pmatrix} a_{11} & b_{11} & h_{Tx=0,Ty=0} \\ a_{12} & b_{12} & k_{Tx=0,Ty=0} \\ a_{13} & b_{13} & l_{Tx=0,Ty=0} \end{pmatrix}$$

Equation (10)

Meanwhile, a process for normalizing the size of column elements of each matrix in each stage for equation (5), equation (6), equation (7), and equation (8) is required. The difference between equation (6) and equation (7) is that equation (6) is a matrix without orthogonality while equation (7) is a matrix with orthogonality. Thus, equation (6) itself cannot reduce a measurement error and the orthogonality of the misorientation matrix can be improved through the subsequent step.

Obtaining of the Misorientation Matrix Between Two Crystals (S40)

In this step, the misorientation matrix is established between the grains using the relationship between the crystal axes and the tilt axes established by equation (5), equation (6) or equation (7). The misorientation matrix between two grains can be established by using the relationship between the crystal axes and the tilt axes with respect to the grains 'A' and 'B' as described above as follows:

$$(c_A D c_B) = (c_A M t)(c_B M t)^{-1}$$

Equation (11)

Namely, the misorientation matrix can be configured for each grain boundary desired to be observed based on equation (11).

Revealing of the Characteristics of Grain Boundaries from the Obtained Misorientation Matrix (S50)

Here, the characteristics of the grain boundaries are revealed from data known in a document about the misorientation matrix configured by equation (8). For example, whether or not the grain boundary is a CSL (Coincident Site Lattice) grain boundary or what kind of CSL grain boundary it is can be discriminated. In detail, misorientation matrix is configured from an axis-angle pair according to indices of the CSL, namely, Σ values (Σ3, Σ5, Σ7, . . . ), reported in the document. In the following step, the product of the inverse matrices of the misorientation matrix measured in the present invention and the misorientation matrix configured from the CSL grain boundary data are calculated. A value calculated from a diagonal component of the calculated matrix, namely, $\theta_d$=a cos [0.5($a_{11}$+$a_{22}$+$a_{33}$−1)], is obtained, and if the value is smaller than that of the reference Σ (e.g., Brandon criteria) known in the document, the Σ value is adopted, and if the value is larger than that of the reference Σ value, the Σ value is rejected. This process is performed in consideration of all the 24 symmetries of the cubic system.

As the present invention may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

What is claimed is:

1. An apparatus for measuring the orientation relationship between neighboring grains and characteristics of grain boundaries by using a goniometer of a transmission electron microscope, the apparatus comprising:
   a goniometer mounted at the transmission electron microscope; and
   a measurement unit for revealing the characteristics of grain boundaries of a specimen by linear-algebraically interpreting a relationship between crystal axes and tilt axes of the specimen using the goniometer;
   wherein, the relationship between the crystal axes and the tilt axes of the specimen is related to a first interplanar angle $\theta_1$, a second interplanar angle $\theta_2$, and a third interplanar angle $\theta_3$ between a first crystal axis H4 desired to be estimated and respectively measured crystal axes H1, H2, H3 after disposing the measured crystal axes of H1, H2, H3 with respect to coordinates formed by a Tx axis and a Ty axis that is perpendicular to an X tilting axis and a Y tilting axis of the goniometer mounted on a transmission electron microscope;
   wherein, the first crystal axis H4 is calculated by $$\begin{pmatrix} h'_1 & k'_1 & l'_1 \\ h'_2 & k'_2 & l'_2 \\ h'_3 & k'_3 & l'_3 \end{pmatrix} \begin{pmatrix} h \\ k \\ 1 \end{pmatrix} = \begin{pmatrix} \cos\theta_1 \\ \cos\theta_2 \\ \cos\theta_3 \end{pmatrix}$$

wherein h'i=hi/$\sqrt{hi^2+ki^2+li^2}$, k'i=ki/$\sqrt{hi^2+ki^2+li^2}$, l'i=li/$\sqrt{hi^2+ki^2+li^2}$, i=1 2, 3;

wherein the first, second, and third interplanar angles of $\theta_1$, $\theta_2$, and $\theta_3$ have a relationship with tilt angles described by:

$$\begin{pmatrix} \cos\theta_1 \\ \cos\theta_2 \\ \cos\theta_3 \end{pmatrix} = \begin{pmatrix} \cos\Delta Tx_1 + \cos\Delta Ty_1 - 1 \\ \cos\Delta Tx_2 + \cos\Delta Ty_2 - 1 \\ \cos\Delta Tx_3 + \cos\Delta Ty_3 - 1 \end{pmatrix} ; \text{and}$$

wherein differences between (Tx$_1$,Ty$_1$) correspond to crystal axis H(A)1(h$_1$k$_1$l$_1$), differences between (Tx$_2$,Ty$_2$) correspond to crystal axis H(A)2(h$_2$k$_2$l$_2$), and differences between (Tx$_3$,Ty$_3$) correspond to crystal axis H(A)3(h$_3$k$_3$l$_3$).

2. A method for measuring the orientation relationship between neighboring grains and characteristics of grain boundaries by using a goniometer of a transmission electron microscope, the method comprising:
   measuring crystal axes H1, H2, and H3 by using the goniometer;
   comparing measured interplanar angles among the crystal axes of H1, H2, and H3 measured with (Tx, Ty) angle pairs of the goniometer mounted at the transmission electron microscope and crystallographically calculated interplanar angles among the crystal axes of H1, H2, and H3;
   selecting a (Tx, Ty) angle pair at which a difference between the measured interplanar angles and the crystallographically calculated interplanar angles is minimized;
   establishing relationship between tilt axes and the crystal axes;
   obtaining a misorientation matrix between two crystals; and
   revealing the characteristics of a grain boundary by using the misorientation matrix;
   wherein, the relationship between the crystal axes and the tilt axes of the specimen is related to a first interplanar angle $\theta_1$, a second interplanar angle $\theta_2$ and a third interplanar angle $\theta_3$ between a first crystal axis H4 desired to be estimated and respectively measured crystal axes H1, H2, and H3 after disposing the measured crystal axes of H1, H2, and H3 with respect to coordinates formed by a Tx axis and a Ty axis that is perpendicular to an X tilting axis and a Y tilting axis of goniometer mounted on a transmission electron microscope;
   wherein, the first crystal axis H4 is calculated by $$\begin{pmatrix} h'_1 & k'_1 & l'_1 \\ h'_2 & k'_2 & l'_2 \\ h'_3 & k'_3 & l'_3 \end{pmatrix} \begin{pmatrix} h \\ k \\ 1 \end{pmatrix} = \begin{pmatrix} \cos\theta_1 \\ \cos\theta_2 \\ \cos\theta_3 \end{pmatrix}$$

wherein h' i=hi/$\sqrt{hi^2+ki^2+li^2}$, k'i=ki/$\sqrt{hi^2+ki^2+li^2}$, l'i=li/$\sqrt{hi^2+ki^2+li^2}$, i=1 2, 3;

wherein the first, second and third interplanar angles of $\theta_1$, $\theta_2$ and $\theta_3$ have a relationship with tilt angles described by:

$$\begin{pmatrix} \cos\theta_1 \\ \cos\theta_2 \\ \cos\theta_3 \end{pmatrix} = \begin{pmatrix} \cos\Delta Tx_1 + \cos\Delta Ty_1 - 1 \\ \cos\Delta Tx_2 + \cos\Delta Ty_2 - 1 \\ \cos\Delta Tx_3 + \cos\Delta Ty_3 - 1 \end{pmatrix} ; \text{and}$$

wherein differences between (Tx$_1$,Ty$_1$) correspond to crystal axis H(A)1(h$_1$k$_1$l$_1$), differences between (Tx$_2$,Ty$_2$) correspond to crystal axis H(A)2(h$_2$k$_2$l$_2$), and differences between (Tx$_3$,Ty$_3$) correspond to crystal axis H(A)3(h$_3$k$_3$l$_3$).

3. The method of claim 2, wherein selecting of the (Tx, Ty) angle pair comprises:
   obtaining an angle ($\gamma$) inclined from a beam center, using the following equation, if the measured interplanar angles among the crystal axes of H1, H2, and H3 are inclined by a tilt angle ($\alpha$) along the Tx axis and by a tilt angle ($\beta$) along the Ty axis using the measured (Tx, Ty) angle pairs:

cos $\gamma$=cos $\alpha$+cos $\beta$−1; and determining indices of the measured crystal axes of H1, H2, and H3 and calculating interplanar angles of a cubic system crystallographically.

4. The method of claim 2, wherein the establishing of the relationship between the tilt angles and the crystal axes comprises:
   arranging a (Tx=90, Ty=0) crystal axis to be parallel with a Tx[100] tilt axis, arranging a (Tx=0, Ty=90) crystal axis to be parallel with a Ty[010] tilt axis, and arranging a (Tx=0, Ty=0) crystal axis to be parallel with a Tz[001] tilt axis according to the following:

$$(c_i \text{Mt}) = \begin{pmatrix} h_{Tx=90,Ty=0} & h_{Tx=0,Ty=90} & h_{Tx=0,Ty=0} \\ k_{Tx=90,Ty=0} & k_{Tx=0,Ty=90} & k_{Tx=0,Ty=0} \\ l_{Tx=90,Ty=0} & l_{Tx=0,Ty=90} & l_{Tx=0,Ty=0} \end{pmatrix} ; \text{ and}$$

normalizing the arranged crystal axes;

wherein $(h_{Tx=90,Ty=0} \, k_{Tx=90,Ty=0} \, l_{Tx=90,Ty=0})$ indicates indices of crystal plane when Tx=90° and Ty=0°.

5. The method of claim 2, wherein, three axes are comprised of two axes inclined by a certain angle of θ along a Tx axis and along a Ty axis, respectively, and one axis parallel to the Tz[001] tilt axis in establishing the relationship between the tilt axes and the crystal axes.

6. The method of claim 2, wherein, three axes are comprised of two axes obtained by subtracting the crystal axis parallel with the Tz[001] axis from the respective crystal axes rotated by a certain angle of θ along the Tx axis and along the Ty axis, and one axis parallel to the Tz[001] axis in establishing the relationship between the tilt axes and the crystal axes.

7. The method of claim 2, wherein, three axes are composed of two axes which are parallel components to Tx, Ty in vectors obtained by subtracting the crystal axis parallel to the Tz[001] axis from the respective crystal axes rotated by a certain angle of θ along the Tx axis and along the Ty axis, and one axis parallel to the Tz[001] axis in establishing the relationship between the tilt axes and the crystal axes according to:

$$(c_i \text{Mt}) = \begin{pmatrix} a_{11} & b_{11} & h_{Tx=0,Ty=0} \\ a_{12} & b_{12} & k_{Tx=0,Ty=0} \\ a_{13} & b_{13} & l_{Tx=0,Ty=0} \end{pmatrix},$$

wherein $$a_{11} = \frac{h_{Tx=\theta,Ty=0}}{\cos\theta} - h_{Tx=0,Ty=0}$$

$$a_{12} = \frac{k_{Tx=\theta,Ty=0}}{\cos\theta} - k_{Tx=0,Ty=0} -$$

$$a_{13} = \frac{l_{Tx=\theta,Ty=0}}{\cos\theta} - l_{Tx=0,Ty=0}$$

$$b_{11} = \frac{h_{Tx=\theta,Ty=0}}{\cos\theta} - h_{Tx=0,Ty=0}$$

$$b_{12} = \frac{k_{Tx=\theta,Ty=0}}{\cos\theta} - k_{Tx=0,Ty=0} -$$

$$b_{13} = \frac{l_{Tx=\theta,Ty=0}}{\cos\theta} - l_{Tx=0,Ty=0}$$

and wherein $(h_{Tx=\theta,Ty=0} \, k_{Tx=\theta,Ty=0} \, l_{Tx=\theta,Ty=0})$ indicates indices of crystal plane when Tx=θ° and Ty=0°.

8. The method of claim 5, wherein the angle θ is larger than 0 but smaller than 10.

* * * * *